(12) United States Patent
Ishikawa et al.

(10) Patent No.: US 10,980,813 B2
(45) Date of Patent: Apr. 20, 2021

(54) ANTIFUNGAL COMPOSITION

(71) Applicant: SEED RESEARCH INSTITUTE CO., LTD., Kunigami (JP)

(72) Inventors: Teruhiko Ishikawa, Okayama (JP); Morita Iwami, Kunigami (JP)

(73) Assignee: SEED RESEARCH INSTITUTE CO., LTD., Kunigami (JP)

( * ) Notice: Subject to any disclaimer, the term of this patent is extended or adjusted under 35 U.S.C. 154(b) by 0 days.

(21) Appl. No.: 16/307,402

(22) PCT Filed: Feb. 27, 2018

(86) PCT No.: PCT/JP2018/007224
§ 371 (c)(1),
(2) Date: Dec. 5, 2018

(87) PCT Pub. No.: WO2018/155706
PCT Pub. Date: Aug. 30, 2018

(65) Prior Publication Data
US 2019/0216820 A1   Jul. 18, 2019

(30) Foreign Application Priority Data

Feb. 27, 2017 (JP) .............................. JP2017-035508

(51) Int. Cl.
*A61K 31/549* (2006.01)
*A61K 31/433* (2006.01)
*A61P 31/10* (2006.01)

(52) U.S. Cl.
CPC .......... *A61K 31/549* (2013.01); *A61K 31/433* (2013.01); *A61P 31/10* (2018.01)

(58) Field of Classification Search
CPC .................................................. A61K 31/549
USPC ..................................................... 514/222.5
See application file for complete search history.

(56) References Cited

U.S. PATENT DOCUMENTS 3,373,158 A * 3/1968 Schorr ................. C07D 285/34
544/8

FOREIGN PATENT DOCUMENTS

NL           6502106 A *  8/1965 ........... C07D 285/34
WO  WO-2006113432 A2 * 10/2006 ........... C07D 417/04

* cited by examiner

*Primary Examiner* — Kahsay Habte
(74) *Attorney, Agent, or Firm* — Leydig, Voit & Mayer, Ltd.

(57) ABSTRACT

Provided is an antifungal composition containing a cyclic N-sulfonylamine compound, a cyclic N-sulfonylimine compound or a cyclic N-sulfonyloxaziridine compound, each having an antifungal activity, as an active ingredient. An antifungal composition containing a compound represented by the formula (1):

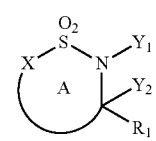

(1)

wherein
ring A is an optionally further substituted 5- to 7-membered heterocycle, and the 5- to 7-membered heterocycle is optionally condensed with 1 or 2 rings selected from an optionally substituted benzene ring and an optionally substituted 5- to 7-membered heterocycle,
X is —N=, —NR$_2$— or —O—;
Y$_1$ is a hydrogen atom, and Y$_2$ is a hydroxy group or Y$_1$ and Y$_2$ may be joined to form a bond or —O—;
R$_1$ is a hydrogen atom, an optionally substituted hydrocarbon group or an optionally substituted heterocyclic group; and
R$_2$ is a hydrogen atom or an optionally substituted hydrocarbon group,
or a salt thereof as an active ingredient.

20 Claims, No Drawings

ANTIFUNGAL COMPOSITION

CROSS-REFERENCE TO RELATED APPLICATIONS

This patent application is the U.S. national phase of International Patent Application No. PCT/JP2018/007224, filed Feb. 27, 2018, which claims the benefit of Japanese Patent Application No. 2017-035508, filed on Feb. 27, 2017, which are incorporated by reference in their entireties herein.

TECHNICAL FIELD

The present invention relates to an antifungal composition containing a cyclic N-sulfonylamine compound, a cyclic N-sulfonylimine compound or a cyclic N-sulfonyloxaziridine compound.

BACKGROUND ART

In recent years, along with an increase in elderly people, progress of advanced medicine, immunodeficiency of late stage cancer patients and the like, infections with fungi have been increasing. These infections provide serious effects, often causing death. Since there are not many kinds of existing antifungal agents, and their toxicity is high, the mother nucleus of a new antifungal agent, which is different from that of conventional medicaments, has been desired. In addition, since the use of antifungal agents causes increased emergence of resistant bacteria, the development of a new medicament has been earnestly desired. While candin-based antifungal agents show low toxicity, since the molecular weight thereof is large, reactivity with serum poses problems. Azole-based antifungal agents have a problem in that administration at a high concentration is difficult in view of the toxicity thereof. Therefore, an effective, low-molecular-weight compound showing low reactivity with serum and low toxicity has been strongly desired.

SUMMARY OF THE INVENTION

Problems to be Solved by the Invention

An object of the present invention is to provide an antifungal composition containing a cyclic N-sulfonylamine compound, a cyclic N-sulfonylimine compound or a cyclic N-sulfonyloxaziridine compound, each having an antifungal activity, as an active ingredient.

Means of Solving the Problems

The present inventors have conducted intensive studies in an attempt to solve the above-mentioned problems and found that a cyclic N-sulfonylamine compound, a cyclic N-sulfonylimine compound or a cyclic N-sulfonyloxaziridine compound, which is represented by the following formula (1), has an antifungal activity, which resulted in the completion of the present invention.

Therefore, the present invention provides the following.

[1] An antifungal composition comprising a compound represented by the formula (1):

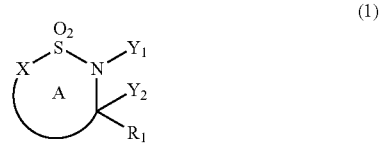

wherein
ring A is an optionally further substituted 5- to 7-membered heterocycle, and the 5- to 7-membered heterocycle is optionally condensed with 1 or 2 rings selected from an optionally substituted benzene ring and an optionally substituted 5- to 7-membered heterocycle,
X is $-N=$, $-NR_2-$ or $-O-$;
$Y_1$ is a hydrogen atom, and $Y_2$ is a hydroxy group or $Y_1$ and $Y_2$ may be joined to form a bond or $-O-$;
$R_1$ is a hydrogen atom, an optionally substituted hydrocarbon group or an optionally substituted heterocyclic group; and
$R_2$ is a hydrogen atom or an optionally substituted hydrocarbon group
(sometimes to be abbreviated as "compound (1)" in the present specification) or a salt thereof as an active ingredient.

[2] The antifungal composition of [1], wherein the compound represented by the formula (1) is a compound represented by the following formula:

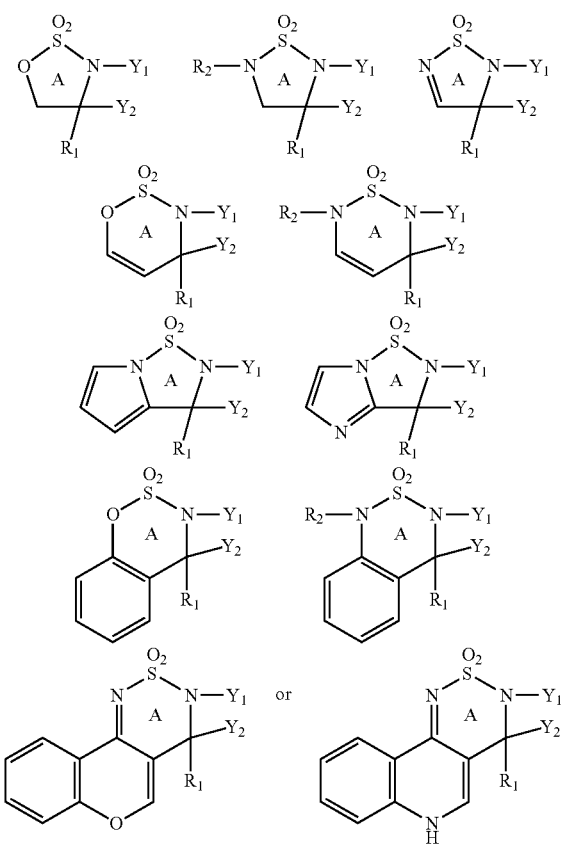

wherein each symbol is as defined in [1].

[3] The antifungal composition of [1] or [2], wherein $Y_1$ is a hydrogen atom and $Y_2$ is a hydroxy group.

[4] The antifungal composition of [1] or [2], wherein $Y_1$ and $Y_2$ are joined to show a bond.

[5] The antifungal composition of [1] or [2], wherein $Y_1$ and $Y_2$ are joined to show —O—.

Effect of the Invention

According to the present invention, an antifungal composition containing a cyclic N-sulfonylamine compound, a cyclic N-sulfonylimine compound or a cyclic N-sulfonyloxaziridine compound, each having an antifungal activity, as an active ingredient is provided.

DESCRIPTION OF EMBODIMENTS

The definition of each substituent used in the present specification is described in detail below. Unless particularly indicated, each substituent has the following definition.

Examples of the "hydrocarbon group" of the "optionally substituted hydrocarbon group" include $C_{1-20}$ alkyl group, $C_{2-20}$ alkenyl group, $C_{2-20}$ alkynyl group, $C_{3-20}$ cycloalkyl group, $C_{3-20}$ cycloalkenyl group, $C_{6-20}$ aryl group, and $C_{7-20}$ aralkyl group.

Examples of the "$C_{1-20}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl, heptyl, octyl.

Examples of the "$C_{2-20}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

Examples of the "$C_{2-20}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and 4-methyl-2-pentynyl. The "$C_{2-20}$ alkynyl group" is preferably a "$C_{2-6}$ alkynyl group".

Examples of the "$C_{3-20}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, and adamantyl. The "$C_{3-20}$ cycloalkyl group" is preferably a "$C_{3-10}$ cycloalkyl group".

Examples of the "$C_{3-20}$ cycloalkenyl group" include cyclopropenyl, cyclobutenyl, cyclopentenyl, cyclohexenyl, cycloheptenyl, and cyclooctenyl.

Examples of the "$C_{6-20}$ aryl group" include phenyl, 1-naphthyl, 2-naphthyl, 1-anthryl, 2-anthryl, and 9-anthryl. The "$C_{6-20}$ aryl group" is preferably a "$C_{6-14}$ aryl group".

Examples of the "$C_{7-20}$ aralkyl group" include benzyl, phenethyl, naphthylmethyl, and phenylpropyl.

Examples of the "heterocyclic group" of the "optionally substituted heterocyclic group" include (i) aromatic heterocyclic group, (ii) non-aromatic heterocyclic group and (iii) 7- to 10-membered crosslinked heterocyclic group, each containing, as a ring-constituting atom besides carbon atom, 1 to 4 hetero atoms selected from nitrogen atom, sulfur atom and oxygen atom.

Examples of the "aromatic heterocyclic group" include a 5- to 14-membered (preferably 5- to 10-membered) aromatic heterocyclic group containing, as a ring-constituting atom besides carbon atom, 1 to 4 hetero atoms selected from nitrogen atom, sulfur atom and oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered condensed polycyclic (preferably di- or tricyclic) aromatic heterocyclic groups such as benzothiophenyl, benzofuranyl, benzimidazolyl, benzoxazolyl, benzoisoxazolyl, benzothiazolyl, benzoisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acrydinyl, phenazinyl, phenothiazinyl, phenoxazinyl and the like.

Examples of the "non-aromatic heterocyclic group" include a 3- to 14-membered (preferably 4- to 10-membered) non-aromatic heterocyclic group containing, as a ring-constituting atom besides carbon atom, 1 to 4 hetero atoms selected from nitrogen atom, sulfur atom and oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered condensed polycyclic (preferably di- or tricyclic) non-aromatic heterocyclic groups such as dihydrobenzofuranyl, dihydrobenzoimidazolyl, dihydrobenzooxazolyl, dihydrobenzothiazolyl, dihydrobenzoisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzoazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

Preferable examples of the "7- to 10-membered crosslinked heterocyclic group" include quinuclidinyl, and 7-azabicyclo[2.2.1]heptanyl.

Examples of the "substituent" of the "optionally substituted hydrocarbon group" and "optionally substituted heterocyclic group" include the following:
(1) halogen atom,
(2) nitro group,
(3) cyano group,
(4) oxo group,
(5) hydroxy group,
(6) optionally substituted $C_{1-6}$ alkoxy group,
(7) optionally substituted $C_{6-14}$ aryloxy group,
(8) optionally substituted $C_{7-16}$ aralkyloxy group,
(9) optionally substituted aromatic heterocyclyl-oxy group,

(10) optionally substituted non-aromatic heterocyclyl-oxy group,
(11) optionally substituted $C_{1-6}$ alkyl-carbonyloxy group,
(12) optionally substituted $C_{6-14}$ aryl-carbonyloxy group,
(13) optionally substituted $C_{1-6}$ alkoxy-carbonyloxy group,
(14) optionally substituted mono- or di-$C_{1-6}$ alkyl-carbamoyloxy group,
(15) optionally substituted $C_{6-14}$ aryl-carbamoyloxy group,
(16) optionally substituted 5- to 14-membered aromatic heterocyclyl-carbonyloxy group,
(17) optionally substituted 3- to 14-membered non-aromatic heterocyclyl-carbonyloxy group,
(18) optionally substituted $C_{1-6}$ alkylsulfonyloxy group,
(19) optionally substituted $C_{6-14}$ arylsulfonyloxy group,
(20) optionally substituted $C_{1-6}$ alkylthio group,
(21) optionally substituted 5- to 14-membered aromatic heterocyclic group,
(22) optionally substituted 3- to 14-membered non-aromatic heterocyclic group,
(23) formyl group,
(24) carboxy group,
(25) optionally substituted $C_{1-6}$ alkyl-carbonyl group,
(26) optionally substituted $C_{6-14}$ aryl-carbonyl group,
(27) optionally substituted 5- to 14-membered aromatic heterocyclyl-carbonyl group,
(28) optionally substituted 3- to 14-membered non-aromatic heterocyclyl-carbonyl group,
(29) optionally substituted $C_{1-6}$ alkoxy-carbonyl group,
(30) optionally substituted $C_{6-14}$ aryloxy-carbonyl group,
(31) optionally substituted $C_{7-16}$ aralkyloxy-carbonyl group,
(32) carbamoyl group,
(33) thiocarbamoyl group,
(34) optionally substituted mono- or di-$C_{1-6}$ alkyl-carbamoyl group,
(35) optionally substituted $C_{6-14}$ aryl-carbamoyl group,
(36) optionally substituted 5- to 14-membered aromatic heterocyclyl-carbamoyl group,
(37) optionally substituted 3- to 14-membered non-aromatic heterocyclyl-carbamoyl group,
(38) optionally substituted $C_{1-6}$ alkylsulfonyl group,
(39) optionally substituted $C_{6-14}$ arylsulfonyl group,
(40) optionally substituted 5- to 14-membered aromatic heterocyclyl-sulfonyl group,
(41) optionally substituted $C_{1-6}$ alkylsulfinyl group,
(42) optionally substituted $C_{6-14}$ arylsulfinyl group,
(43) optionally substituted 5- to 14-membered aromatic heterocyclyl-sulfinyl group,
(44) amino group,
(45) optionally substituted mono- or di-$C_{1-6}$ alkylamino group,
(46) optionally substituted mono- or di-$C_{6-14}$ arylamino group,
(47) optionally substituted 5- to 14-membered aromatic heterocyclyl-amino group,
(48) optionally substituted $C_{7-16}$ aralkylamino group,
(49) formylamino group,
(50) optionally substituted $C_{1-6}$ alkyl-carbonylamino group,
(51) optionally substituted ($C_{1-6}$ alkyl) ($C_{1-6}$ alkyl-carbonyl) amino group,
(52) optionally substituted $C_{6-14}$ aryl-carbonylamino group,
(53) optionally substituted $C_{1-6}$ alkoxy-carbonylamino group,
(54) optionally substituted $C_{7-16}$ aralkyloxy-carbonylamino group,
(55) optionally substituted $C_{1-6}$ alkylsulfonylamino group,
(56) optionally substituted $C_{6-14}$ arylsulfonylamino group,
(57) optionally substituted $C_{1-6}$ alkyl group,
(58) optionally substituted $C_{2-6}$ alkenyl group,
(59) optionally substituted $C_{2-6}$ alkynyl group,
(60) optionally substituted $C_{3-10}$ cycloalkyl group,
(61) optionally substituted $C_{3-10}$ cycloalkenyl group, and
(62) optionally substituted $C_{6-14}$ aryl group.

The number of the above-mentioned "substituent" of the "optionally substituted hydrocarbon group" and "optionally substituted heterocyclic group" is, for example, 1 to 5, preferably 1 to 3. When the number of the substituents is two or more, the respective substituents may be the same or different.

The definition of each symbol in the formula (1) is described in detail below.

Ring A is an optionally further substituted 5- to 7-membered heterocycle, and the 5- to 7-membered heterocycle is optionally condensed with 1 or 2 rings selected from an optionally substituted benzene ring and an optionally substituted 5- to 7-membered heterocycle.

The "5- to 7-membered heterocycle" of the "optionally further substituted 5- to 7-membered heterocycle" for ring A is a 5- to 7-membered heterocycle containing, as ring constituent atoms besides carbon atom, nitrogen atom, sulfur atom, and nitrogen atom or oxygen atom for X.

The "5- to 7-membered heterocycle" of the "optionally further substituted 5- to 7-membered heterocycle" for ring A is optionally further substituted at substitutable positions by 1 to 6 (preferably 1 to 3, more preferably 1 or 2) substituents other than $R_1$, $R_2$, $Y_1$ and $Y_2$ groups. As such substituent, optionally substituted $C_{1-20}$ alkyl group (e.g., methyl, ethyl) and optionally substituted $C_{7-20}$ aralkyl group (e.g., phenylethyl) are preferable, $C_{1-20}$ alkyl group (e.g., methyl, ethyl), and $C_{7-20}$ aralkyl group (e.g., phenylethyl) optionally substituted by 1 to 3 halogen atoms (e.g., chlorine atom) are more preferable. When a plurality of substituents are present, each substituent may be the same or different.

As the "5- to 7-membered heterocycle" of the "optionally substituted 5- to 7-membered heterocycle" which is optionally condensed with the "optionally further substituted 5- to 7-membered heterocycle" for ring A, 5-membered heterocycle (e.g., pyrrole ring, imidazole ring), 6-membered heterocycle (e.g., dihydropyridine ring, pyran ring), and 7-membered heterocycle (e.g., azepane ring, oxepane ring) are preferable.

As the "substituent" of the "optionally substituted benzene ring" or "optionally substituted 5- to 7-membered heterocycle" optionally condensed with "optionally further substituted 5- to 7-membered heterocycle" for ring A, halogen atoms (e.g., fluorine atom, chlorine atom, bromine atom), nitro group, cyano group, optionally substituted $C_{1-6}$ alkoxy group (e.g., methoxy), and optionally substituted $C_{1-6}$ alkoxy-carbonyl group (e.g., methoxycarbonyl) are preferable, halogen atoms (e.g., fluorine atom, chlorine atom, bromine atom), nitro group, cyano group, $C_{1-6}$ alkoxy group (e.g., methoxy), and $C_{1-6}$ alkoxy-carbonyl group (e.g., methoxycarbonyl) are more preferable.

Ring A is
preferably, a 5- to 7-membered heterocycle containing, as a ring-constituting atom besides carbon atoms, nitrogen atom, sulfur atom, and nitrogen atom or oxygen atom for X, which is optionally further substituted by 1 to 6 (preferably 1 to 3, more preferably 1 or 2) substituents selected from an optionally substituted $C_{1-20}$ alkyl group (e.g., methyl, ethyl) and an optionally substituted $C_{7-20}$ aralkyl group (e.g., phenylethyl), and the 5- to 7-membered heterocycle is optionally condensed with 1 or 2 rings selected from a benzene ring, a 5-membered heterocycle (e.g., pyrrole ring, imidazole ring) and a 6-membered heterocycle (e.g., dihydropyridine ring, pyran ring) optionally substituted by 1 to 6 (preferably 1 to 3, more preferably 1 or 2) substituents selected from a halogen atom (e.g., fluorine atom, chlorine atom, bromine atom), a nitro group, a cyano group, an optionally substituted $C_{1-6}$ alkoxy group (e.g., methoxy) and an optionally substituted $C_{1-6}$ alkoxy-carbonyl group (e.g., methoxycarbonyl), more preferably, a 5- to 7-membered heterocycle containing, as a ring-constituting atom besides carbon atoms, nitrogen atom, sulfur atom, and nitrogen atom or oxygen atom for X, which is optionally further substituted by 1 to 6 (preferably 1 to 3, more preferably 1 or 2) substituents selected from a $C_{1-20}$ alkyl group (e.g., methyl, ethyl) and a $C_{7-20}$ aralkyl group (e.g., phenylethyl) optionally substituted by 1 to 3 halogen atoms (e.g., chlorine atom), and the 5- to 7-membered heterocycle is optionally condensed with 1 or 2 rings selected from a benzene ring, a 5-membered heterocycle (e.g., pyrrole ring, imidazole ring) and a 6-membered heterocycle (e.g., dihydropyridine ring, pyran ring) optionally substituted by 1 to 6 (preferably 1 to 3, more preferably 1 or 2) substituents selected from a halogen atom (e.g., fluorine atom, chlorine atom, bromine atom), a nitro group, a cyano group, a $C_{1-6}$ alkoxy group (e.g., methoxy) and a $C_{1-6}$ alkoxy-carbonyl group (e.g., methoxycarbonyl).

X is —N=, —NR$_2$— or —O—, and R$_2$ is a hydrogen atom or an optionally substituted hydrocarbon group.

As the "hydrocarbon group" of the "optionally substituted hydrocarbon group" for R$_2$, a $C_{1-20}$ alkyl group (e.g., octyl) is preferable, and as the "substituent" thereof, an optionally substituted $C_{6-20}$ aryl group (e.g., dichlorophenyl) is preferable. R$_2$ is preferably a hydrogen atom or an optionally substituted $C_{1-20}$ alkyl group (e.g., octyl), more preferably, a hydrogen atom or a $C_{1-20}$ alkyl group (e.g., octyl).

X is preferably —N=, —NH—, —N(optionally substituted $C_{1-20}$ alkyl)- or —O—, more preferably, —N=, —NH—, —N($C_{1-20}$ alkyl)- or —O—.

Y$_1$ is a hydrogen atom, and Y$_2$ is a hydroxy group, or Y$_1$ and Y$_2$ are joined to form a bond or —O—.

When Y$_1$ is a hydrogen atom and Y$_2$ is a hydroxy group, the formula (1) is the following formula (1-1). When Y$_1$ and Y$_2$ are joined to form a bond, the formula (1) is the following formula (1-2), and when Y$_1$ and Y$_2$ are joined to form —O—, the formula (1) is the following formula (1-3).

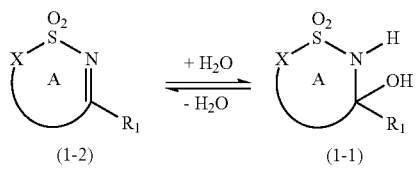
(1-2)  (1-1)

R$_1$ is a hydrogen atom, an optionally substituted hydrocarbon group or an optionally substituted heterocyclic group.

As the "hydrocarbon group" of the "optionally substituted hydrocarbon group" for R$_1$, a $C_{1-20}$ alkyl group (e.g., methyl, ethyl) or a $C_{6-20}$ aryl group (e.g., phenyl) is preferable. As the "substituent" thereof, a halogen atom (e.g., chlorine atom) is preferable.

As the "heterocyclic group" of the "optionally substituted heterocyclic group" for R$_1$, a 5- or 6-membered aromatic heterocyclic group (e.g., isoxazolyl, imidazolyl) is preferable. As the "substituent" thereof, a halogen atom (e.g., chlorine atom) is preferable.

R$_1$ is preferably a hydrogen atom, an optionally substituted $C_{1-20}$ alkyl group (e.g., methyl, ethyl) or an optionally substituted $C_{6-20}$ aryl group (e.g., phenyl), more preferably, a hydrogen atom, a $C_{1-20}$ alkyl group (e.g., methyl, ethyl) or a $C_{6-20}$ aryl group (e.g., phenyl) optionally substituted by 1 to 3 halogen atoms (e.g., chlorine atom).

In one embodiment of the present invention, compound (1) is preferably a compound represented by the following formula:

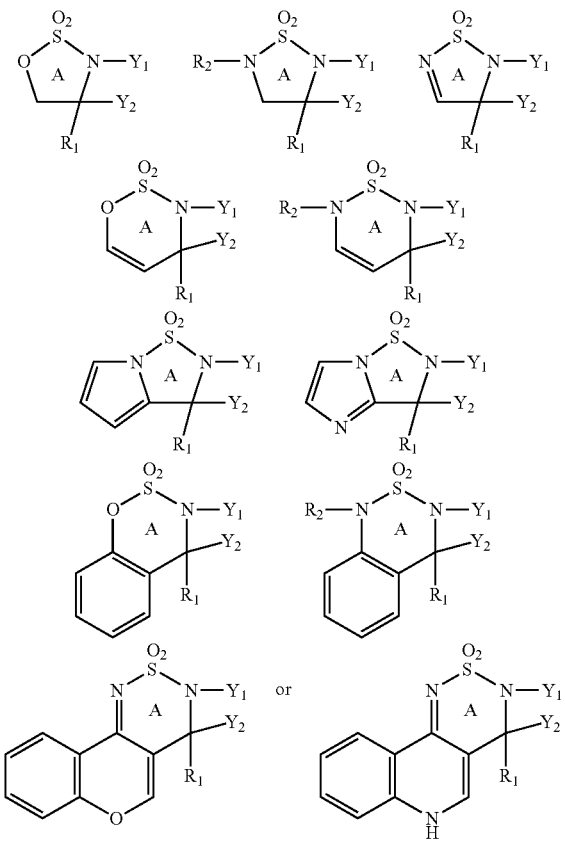

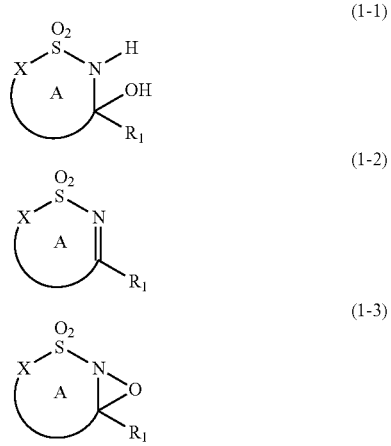

A compound represented by the formula (1-2) is in equilibrium with a compound represented by the formula (1-1) in a solution in the presence of water.

wherein each symbol is as defined above.

Preferable examples of compound (1) include the following compounds.

[Compound 1-1]

Compound (1) wherein ring A is a 5- to 7-membered heterocycle containing, as a ring-constituting atom besides carbon atoms, nitrogen atom, sulfur atom, and nitrogen atom or oxygen atom for X, which is optionally further substituted by 1 to 6 (preferably 1 to 3, more preferably 1 or 2) substituents selected from an optionally substituted $C_{1-20}$ alkyl group (e.g., methyl, ethyl) and an optionally substituted $C_{7-20}$ aralkyl group (e.g., phenylethyl), and the 5- to 7-membered heterocycle is optionally condensed with 1 or 2 rings selected from a benzene ring, a 5-membered heterocycle (e.g., pyrrole ring, imidazole ring) and a 6-membered heterocycle (e.g., dihydropyridine ring, pyran ring) optionally substituted by 1 to 6 (preferably 1 to 3, more preferably 1 or 2) substituents selected from a halogen atom (e.g., fluorine atom, chlorine atom, bromine atom), a nitro group, a cyano group, an optionally substituted $C_{1-6}$ alkoxy group (e.g., methoxy) and an optionally substituted $C_{1-6}$ alkoxycarbonyl group (e.g., methoxycarbonyl);

X is —N=, —NH—, —N(optionally substituted $C_{1-20}$ alkyl)- or —O—;

$Y_1$ is a hydrogen atom, and $Y_2$ is a hydroxy group, or $Y_1$ and $Y_2$ are joined to form a bond or —O—;

$R_1$ is a hydrogen atom, an optionally substituted $C_{1-20}$ alkyl group (e.g., methyl, ethyl) or an optionally substituted $C_{6-20}$ aryl group (e.g., phenyl); and $R_2$ is a hydrogen atom or an optionally substituted $C_{1-20}$ alkyl group (e.g., octyl).

[Compound 1-2]

Compound (1) wherein ring A is a 5- to 7-membered heterocycle containing, as a ring-constituting atom besides carbon atoms, nitrogen atom, sulfur atom, and nitrogen atom or oxygen atom for X, which is optionally further substituted by 1 to 6 (preferably 1 to 3, more preferably 1 or 2) substituents selected from a $C_{1-20}$ alkyl group (e.g., methyl, ethyl) and a $C_{7-20}$ aralkyl group (e.g., phenylethyl) optionally substituted by 1 to 3 halogen atoms (e.g., chlorine atom), and the 5- to 7-membered heterocycle is optionally condensed with 1 or 2 rings selected from a benzene ring, a 5-membered heterocycle (e.g., pyrrole ring, imidazole ring) and a 6-membered heterocycle (e.g., dihydropyridine ring, pyran ring) optionally substituted by 1 to 6 (preferably 1 to 3, more preferably 1 or 2) substituents selected from a halogen atom (e.g., fluorine atom, chlorine atom, bromine atom), a nitro group, a cyano group, a $C_{1-6}$ alkoxy group (e.g., methoxy) and a $C_{1-6}$ alkoxy-carbonyl group (e.g., methoxycarbonyl);

X is —N=, —NH—, —N($C_{1-20}$ alkyl)- or —O—;

$Y_1$ is a hydrogen atom, and $Y_2$ is a hydroxy group, or $Y_1$ and $Y_2$ are joined to form a bond or —O—;

$R_1$ is a hydrogen atom, a $C_{1-20}$ alkyl group (e.g., methyl, ethyl) or a $C_{6-20}$ aryl group (e.g., phenyl) optionally substituted 1 to 3 halogen atoms (e.g., chlorine atom); and $R_2$ is a hydrogen atom or a $C_{1-20}$ alkyl group (e.g., octyl).

[Compound 1-3]

Compound (1) represented by the following formula:

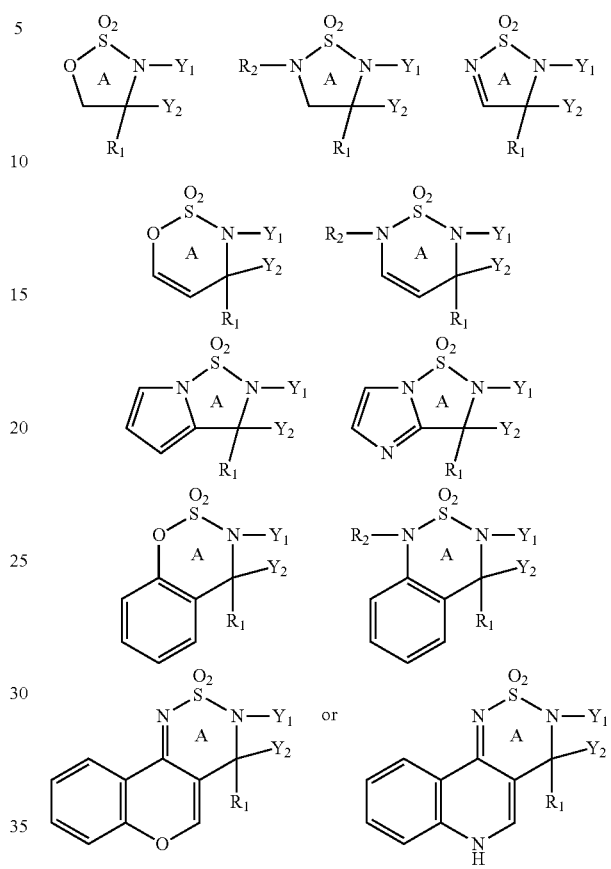

wherein ring A is optionally further substituted by 1 or 2 substituents selected from a $C_{1-20}$ alkyl group (e.g., methyl, ethyl) and a $C_{7-20}$ aralkyl group (e.g., phenylethyl) optionally substituted by 1 to 3 halogen atoms (e.g., chlorine atom);

the ring condensed with ring A is optionally substituted by 1-6 (preferably 1 to 3, more preferably 1 or 2) substituents selected from a halogen atom (e.g., fluorine atom, chlorine atom, bromine atom), a nitro group, a cyano group, a $C_{1-6}$ alkoxy group (e.g., methoxy) and a $C_{1-6}$ alkoxy-carbonyl group (e.g., methoxycarbonyl);

$Y_1$ is a hydrogen atom, and $Y_2$ is a hydroxy group, or $Y_1$ and $Y_2$ are joined to form a bond or —O—;

$R_1$ is a hydrogen atom, a $C_{1-20}$ alkyl group (e.g., methyl, ethyl) or a $C_{6-20}$ aryl group (e.g., phenyl) optionally substituted 1 to 3 halogen atoms (e.g., chlorine atom); and $R_2$ is a hydrogen atom or a $C_{1-20}$ alkyl group (e.g., octyl).

The production method of the compound of the present invention is explained below.

The whole scheme of the production method of the compound of the present invention is shown below.

(1)

-continued

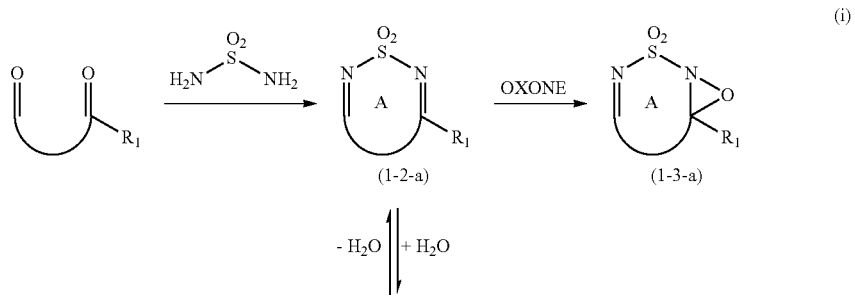

(i)

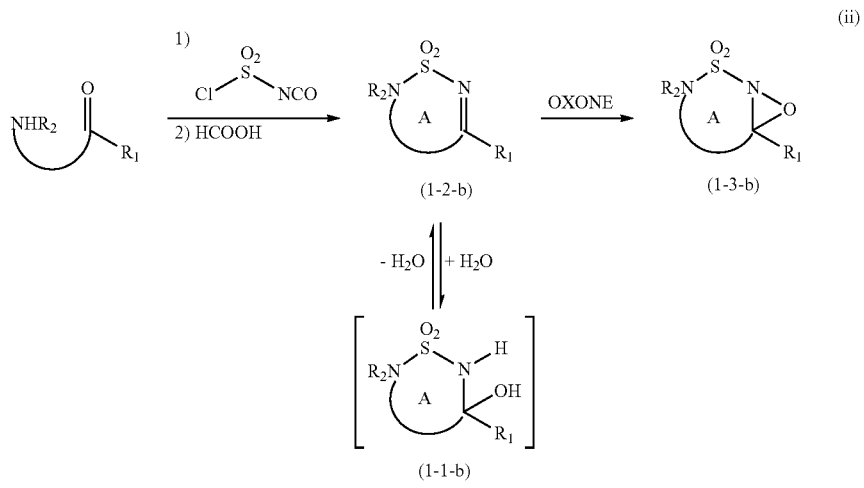

(ii)

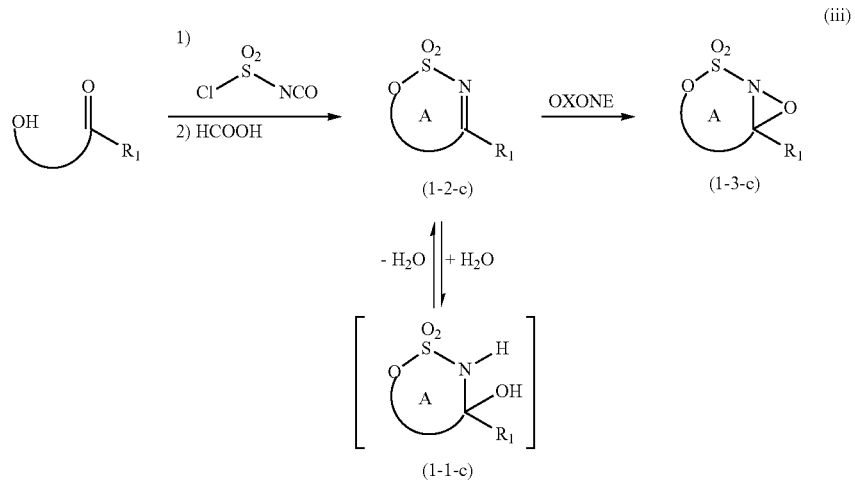

(iii)

wherein ring A, $R_1$ and $R_2$ are as defined above.

(i) When X is —N=, cyclic sulfonylimine (1-2-a) can be obtained by reacting diketone or ketoaldehyde used as a substrate with sulfamide.

Sulfamide can be used at generally 1-5 molar equivalents, preferably 1-2 molar equivalents, relative to diketone or ketoaldehyde. The reaction temperature is generally 0° C.-70° C., preferably 30° C.-50° C. While the reaction time varies depending on the kind of diketone or ketoaldehyde, reaction temperature and the like, it is generally 1-24 hr, preferably 6-10 hr. As the reaction solvent, tetrahydrofuran, ethyl acetate, acetonitrile, dichloroethane, or a mixed solvent thereof and the like can be used, with particular preference given to tetrahydrofuran solvent.

Diketone or ketoaldehyde may be a commercially available product, and can also be produced according to a method known per se or a method analogous thereto.

Cyclic sulfonyloxaziridine (1-3-a) can be obtained by reacting the obtained cyclic sulfonylimine (1-2-a) with OXONE (registered trade mark).

OXONE can be used at generally 1-5 molar equivalents, preferably 1-2 molar equivalents, relative to cyclic sulfonylimine (1-2-a). The reaction temperature is generally 0° C.-50° C., preferably 10° C.-30° C. While the reaction time varies depending on the kind of cyclic sulfonylimine (1-2-a), reaction temperature and the like, it is generally 1-5 hr, preferably 1-2 hr. As the reaction solvent, tetrahydrofuran, ethyl acetate, acetonitrile, dichloroethane, or a mixed solvent thereof and the like can be used, with particular preference given to tetrahydrofuran solvent.

(ii) When X is —NR$_2$—, cyclic sulfonylimine (1-2-b) can be obtained by reacting aminoketone or aminoaldehyde used as a substrate with chlorosulfonyl isocyanate and formic acid.

Chlorosulfonyl isocyanate can be used at generally 1-5 molar equivalents, preferably 1-2 molar equivalents, relative to aminoketone or aminoaldehyde. In addition, formic acid can be used at generally 1-5 molar equivalents, preferably 1-2 molar equivalents, relative to aminoketone or aminoaldehyde. The reaction temperature is generally 0° C.-70° C., preferably 0° C.-30° C. While the reaction time varies depending on the kind of aminoketone or aminoaldehyde, reaction temperature and the like, it is generally 1-12 hr, preferably 3-5 hr. As the reaction solvent, tetrahydrofuran, ethyl acetate, acetonitrile, dichloroethane, or a mixed solvent thereof and the like can be used, with particular preference given to tetrahydrofuran solvent.

Aminoketone or aminoaldehyde may be a commercially available product, and can also be produced according to a method known per se or a method analogous thereto.

Cyclic sulfonyloxaziridine (1-3-b) can be obtained by reacting the obtained cyclic sulfonylimine (1-2-b) with OXONE. This reaction can be performed in the same manner as in the above-mentioned (i) wherein X is —N═.

(iii) When X is —O—, cyclic sulfonylimine (1-2-c) can be obtained by reacting hydroxyketone or hydroxyaldehyde used as a substrate with chlorosulfonyl isocyanate and formic acid.

Chlorosulfonyl isocyanate can be used at generally 1-5 molar equivalents, preferably 1-2 molar equivalents, relative to hydroxyketone or hydroxyaldehyde. In addition, formic acid can be used at generally 1-5 molar equivalents, preferably 1-2 molar equivalents, relative to hydroxyketone or hydroxyaldehyde. The reaction temperature is generally 0° C.-70° C., preferably 0° C.-30° C. While the reaction time varies depending on the kind of hydroxyketone or hydroxyaldehyde, reaction temperature and the like, it is generally 1-12 hr, preferably 3-5 hr. As the reaction solvent, tetrahydrofuran, ethyl acetate, acetonitrile, dichloroethane, or a mixed solvent thereof and the like can be used, with particular preference given to tetrahydrofuran solvent.

Hydroxyketone or hydroxyaldehyde may be a commercially available product, and can also be produced according to a method known per se or a method analogous thereto.

Cyclic sulfonyloxaziridine (1-3-c) can be obtained by reacting the obtained cyclic sulfonylimine (1-2-c) with OXONE. This reaction can be performed in the same manner as in the above-mentioned (i) wherein X is —N═.

The compound and a synthetic intermediate thereof of the present invention may be salts. Examples of such salt include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like. Of these salts, a pharmaceutically acceptable salt is preferable.

The compound of the present invention and a salt thereof have a strong antifungal activity against a broad range of fungi, and are expected to be new antifungal agents. Therefore, a antifungal composition containing the compound or a salt thereof as an active ingredient can be used as a medicament, a pesticide and the like.

Examples of the fungi to be the target of the antifungal composition include, but are not limited to, fungi such as yeast (e.g., *Saccharomyces* etc.), the genus *Candida* (e.g., *Candida albicans, Candida parapsilosis, Candida tropicalis, Candida krusei, Candida glabrata, Candida quilliermondii, Candida lusitaniae* etc.), the genus *Aspergillus* (e.g., *Aspergillus fumigatus, Aspergillus flavus, Aspergillus niger, Aspergillus terreus* etc.), the genus *Trichophyton* (e.g., *Trichophyton rubrum, Trichophyton mentagrophytes, Trichophyton tonsurans, Microsporum canis, Microsporum gypseum, Trichophyton verrucosum* etc.) and the like. Mycosis is not particularly limited, and deep skin mycosis, deep mycosis, mycetoma, and fungemia can be mentioned.

When the antifungal composition is used as a pesticide, the target crop is not particularly limited and, for example, plants such as grain (e.g., rice, barley, wheat, rye, oats, corn, kaoliang etc.), beans (soybean, adzuki bean, broad bean, pea, peanut etc.), fruit-tree, fruits (apple, citrus, pear, grapes, peach, ume (Japanese plum), cherry, walnut, almond, banana, strawberry etc.), vegetables (cabbage, tomato, spinach, broccoli, lettuce, onion, green onion, bell pepper etc.), root vegetables (carrot, potato, sweet potato, radish, lotus root, turnip etc.), crops for processing (cotton, hemp, kozo (paper mulberry), mitsumata plant, rape seed, beet, hop, sugarcane, sugar beet, olive, rubber, coffee, tobacco, tea etc.), gourds (pumpkin, cucumber, watermelon, melon etc.), grasses (orchard grass, sorghum, timothy, clover, alfalfa etc.), sods (Korean lawn grass, bentgrass etc.), crops for flavor etc. (lavender, rosemary, thyme, parsley, pepper, ginger etc.), flowering plants (*chrysanthemum*, rose, orchid etc.) and the like can be mentioned. The antifungal composition can be used for controlling the diseases related to the aforementioned fungi in the crops, by treating the target crop and/or seed of the target crop with an effective amount thereof.

The pesticide can be used at the following form, and generally used together with an adjuvant conventionally used in the pharmaceutical fields. The compound and a salt thereof of the present invention are formulated by a known method into, for example, emulsion stock solution, sprayable paste, sprayable or dilutable solution, dilutable emulsion, wettable agent, water soluble powder, powder, granule, flowable pesticide, dry flowable pesticide, smoking agent, fumigant and, for example, capsule made of a polymer substance.

As additive and carrier when the object is a solid agent, plant-derived powder such as soy flour, wheat flour and the like, mineral fine powder such as diatomaceous earth, apatite, plaster, talc, bentonite, clay and the like, and organic and inorganic compounds such as sodium benzoate, urea, salt cake and the like can be used.

When a liquid dosage form is desired, vegetable oil, mineral oil, kerosene, aromatic hydrocarbons such as xylene and toluene, amides such as formamide, and dimethylformamide, sulfoxides such as dimethyl sulfoxide, ketones such as methyl isobutyl ketone and acetone, trichloroethylene, water and the like are used as solvents. To afford these preparations in a uniform and stable form, a surfactant can also be added where necessary. The thus-obtained wettable agent, emulsion, aqueous solution, flowable pesticide, and dry flowable pesticide are diluted with water to a given concentration to give a suspension or emulsion and used by spraying same on the soil or plant, and powder and granule are used by directly spraying on the soil or plant.

The content and dose of the active ingredient in a pesticide containing the compound and a salt thereof of the present invention can be changed in a wide range depending on the dosage form, the kind of fungi to be the application target, target crop and the like.

On the other hand, when the antifungal composition is used as a medicament, it can be administered to a treatment target, for example, a mammal (e.g., human, mouse, rat, hamster, rabbit, cat, dog, bovine, sheep, monkey etc.) by an oral or parenteral administration route (e.g., intravenous injection, intramuscular injection, subcutaneous administration, rectal administration, transdermal administration).

When the antifungal composition is transdermally administered, it can contain, besides the above-mentioned active ingredient, oily base, emulsifier and emulsion stabilizer, solubilizing agents, powder component, polymer component, adhesiveness improver, film-forming agent, pH adjuster, antioxidant, antiseptic agent, preservative, shape retention agent, humectant, skin protector, algefaciant, flavor, colorant, chelating agent, lubricant, blood circulation promoter, astringent, tissue repair promoter, adiaphoretic, plant extraction component, animal extraction component, anti-inflammatory agent, antipruritic agent and the like as necessary. As these additives, those generally used for preparations can be used.

The antifungal composition can be used by formulating the above-mentioned components other than the active ingredient and the like into external drugs such as cream, liquid, lotion, emulsion, tincture, ointment, aqueous gel, oily gel, aerosol, powder, shampoo, soap, enamel agent for application to nail and the like, by a method conventionally used in the field of pharmaceutical preparations.

When the antifungal composition is orally administered, it can be prepared into a dosage form suitable for oral administration such as capsule, tablet, granule, powder, pill, fine granules, troche and the like. These preparations can be produced using additives generally used for oral preparations, such as excipient, filler, binder, moistening agent, disintegrant, surfactant, lubricant, dispersing agent, buffering agent, preservative, solubilizing agent, antiseptic agent, flavoring agent, soothing agent, stabilizer and the like by a conventional method.

EXAMPLES

The present invention is explained in more detail by referring to the following Examples. These do not limit the present invention, and may be changed within the scope of the present invention.

$^1$H NMR spectra were measured by a nuclear magnetic resonance apparatus (manufactured by Varian, 400 MR), and all δ values are shown in ppm. Mass spectrum was measured by HPLC-Chip/QTOF mass spectrometry system (Agilent Technologies), and m/z values are shown.

Example 1

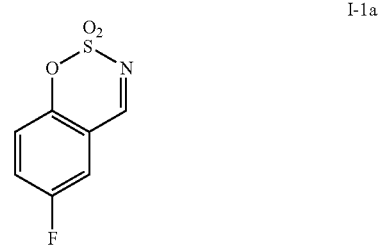 [SMILES: O=S1(=O)N=Cc2cc(F)ccc2O1]

I-1a

4-Fluorosalicylaldehyde (300 mg, 2.14 mmol), triethylamine (0.45 mL, 3.21 mmol), and 4-(dimethylamino)pyridine (26 mg, 0.21 mmol) were dissolved in THF (4 mL), chlorosulfonyl isocyanate (360 mg, 2.57 mmol) was added at 0° C., and the mixture was stirred at room temperature for 3 hr. Formic acid (1.0 mL) and water (1.0 mL) were added at 0° C., and the mixture was stirred at room temperature for 3 hr. Anhydrous sodium sulfate was added to remove water in the reaction system, and the mixture was filtered through cotton. The obtained filtrate was concentrated by a rotary evaporator. The obtained crude product was purified by silica gel column chromatography (solvent: hexane and ethyl acetate) to give cyclic N-sulfonylimine I-1a (321 mg, 1.61 mmol) as a colorless solid (yield 75%).

MS: m/z 202 ([M+1], $C_7H_4FNO_3S$)

$^1$H NMR (CDCl$_3$) δ 7.33 (dd, 1H, J=4.0, 8.8 Hz), 7.39 (dd, 1H, J=3.2, 8.8 Hz), 7.45-7.51 (m, 1H), 8.65 (s, 1H).

Example 2

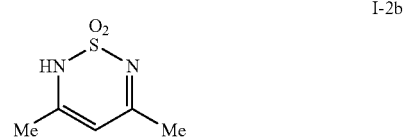

I-2b

Pentane-2,4-dione (300 mg, 0.30 mmol) was dissolved in THF (4 mL), sulfamide (316 mg, 0.33 mmol) and p-toluenesulfonic acid (52 mg, 0.03 mmol) were added, and the mixture was stirred at 50° C. for 6 hr. The reaction mixture was concentrated by a rotary evaporator. The obtained crude product was purified by silica gel column chromatography (solvent: hexane and ethyl acetate) to give cyclic N-sulfonylimine I-2b (387 mg, 0.24 mmol) as a colorless solid (yield 80%).

MS: m/z 161 ([M+1], $C_5H_8N_2O_2S$)

$^1$H NMR (CDCl$_3$) δ 2.23 (s, 6H), 5.69 (s, 1H), 9.10-9.70 (br, 1H).

Example 3

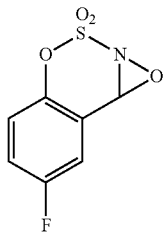

II-1a

Cyclic N-sulfonylimine I-1a (10 mg, 0.05 mmol) was dissolved in THF (3 mL), OXONE (11 mg) and sodium hydrogen carbonate (11 mg) were added, and the mixture was stirred at room temperature for 1 hr. The reaction mixture was filtered through cotton, and the filtrate was concentrated by a rotary evaporator. The obtained crude product was purified by silica gel column chromatography (solvent: hexane and ethyl acetate) to give cyclic N-sulfonyloxaziridine II-1a (6 mg, 0.03 mmol) as a colorless liquid (yield 60%).

MS: m/z 218 ([M+1], $C_7H_4FNO_4S$)

$^1$H NMR (CDCl$_3$) δ 5.37 (s, 1H), 7.22 (dd, 1H, J=4.0, 8.8 Hz), 7.28-7.34 (m, 1H), 7.44 (dd, 1H, J=3.2, 8.8 Hz).

Example 4

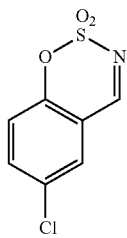

I-1b

Using 4-chlorosalicylaldehyde as a substrate and by a method similar to that in Example 1, cyclic N-sulfonylimine I-1b was synthesized.

MS: m/z 218 ([M+1], $C_7H_4ClNO_3S$)

$^1$H NMR (CDCl$_3$) δ 7.28 (d, 1H, J=8.6 Hz), 7.60-7.80 (m, 2H), 8.63 (s, 1H).

Example 5

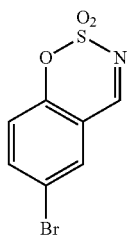

I-1c

Using 4-bromosalicylaldehyde as a substrate and by a method similar to that in Example 1, cyclic N-sulfonylimine I-1c was synthesized.

MS: m/z 262 ([M+1], $C_7H_4BrNO_3S$)

$^1$H NMR (CDCl$_3$) δ 7.20 (d, 1H, J=8.6 Hz), 7.60-7.75 (m, 2H), 8.63 (s, 1H).

Example 6

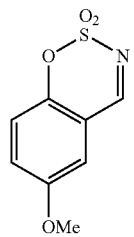

I-1d

Using 4-methoxysalicylaldehyde as a substrate and by a method similar to that in Example 1, cyclic N-sulfonylimine I-1d was synthesized.

MS: m/z 214 ([M+1], $C_8H_7NO_4S$)

$^1$H NMR (CDCl$_3$) δ 3.83 (s, 3H), 7.10 (d, 1H, J=2.6 Hz), 7.20 (d, 1H, J=8.8 Hz), 7.44 (dd, 1H, J=2.6, 8.8 Hz), 8.62 (s, 1H).

Example 7

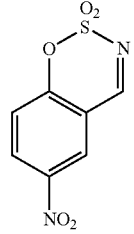

I-1e

Using 4-nitrosalicylaldehyde as a substrate and by a method similar to that in Example 1, cyclic N-sulfonylimine I-1e was synthesized.

MS: m/z 229 ([M+1], $C_7H_4N_2O_5S$)

$^1$H NMR (CDCl$_3$) δ 7.48 (d, 1H, J=8.6 Hz), 8.62 (d, 1H, J=8.6 Hz), 8.63 (s, 1H), 8.80 (s, 1H).

Example 8

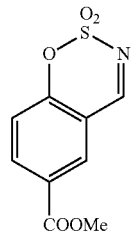

I-1f

Using 4-methoxycarbonylsalicylaldehyde as a substrate and by a method similar to that in Example 1, cyclic N-sulfonylimine I-1f was synthesized.

MS: m/z 242 ([M+1], $C_9H_7NO_5S$)

Example 9

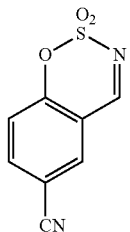

I-1g

Using 4-cyanosalicylaldehyde as a substrate and by a method similar to that in Example 1, cyclic N-sulfonylimine I-1g was synthesized.

MS: m/z 209 ([M+1], $C_8H_4N_2O_3S$)

Example 10

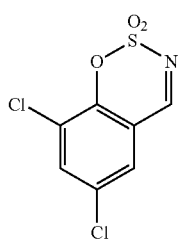

I-1h

Using 2,4-dichlorosalicylaldehyde as a substrate and by a method similar to that in Example 1, cyclic N-sulfonylimine I-1h was synthesized.

MS: m/z 252 ([M+1], $C_7H_3Cl_2NO_3S$)

$^1$H NMR (CDCl$_3$) δ 7.80 (d, 1H, J=2.4 Hz), 7.99 (d, 1H, J=2.4 Hz), 8.83 (s, 1H).

Example 11

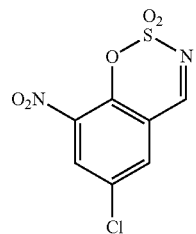

I-1i

Using 2-nitro-4-dichlorosalicylaldehyde as a substrate and by a method similar to that in Example 1, cyclic N-sulfonylimine I-1i was synthesized.

MS: m/z 263 ([M+1], $C_7H_3ClN_2O_5S$)

Example 12

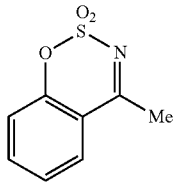

I-1j

Using 2-hydroxyacetophenone as a substrate and by a method similar to that in Example 1, cyclic N-sulfonylimine I-1j was synthesized.

MS: m/z 198 ([M+1], $C_8H_7NO_3S$)

Example 13

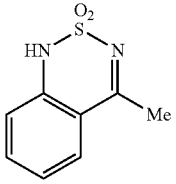

I-1k

Using 2-aminoacetophenone as a substrate and by a method similar to that in Example 1, cyclic N-sulfonylimine I-1k was synthesized.

MS: m/z 197 ([M+1], $C_8H_8N_2O_2S$)

Example 14

I-1l

Using 2-amino-4-chlorobenzophenone as a substrate and by a method similar to that in Example 1, cyclic N-sulfonylimine I-1l was synthesized.

MS: m/z 293 ([M+1], $C_{13}H_9ClN_2O_2S$)

Example 15

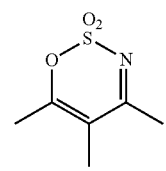

I-2a

Using 3-methylpentane-2,4-dione as a substrate and by a method similar to that in Example 1, cyclic N-sulfonylimine I-2a was synthesized.

MS: m/z 176 ([M+1], $C_6H_9NO_3S$)

Example 16

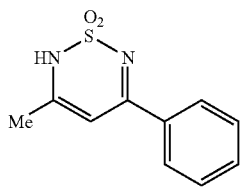
I-2c

Using 1-phenylbutane-1,3-dione as a substrate and by a method similar to that in Example 2, cyclic N-sulfonylimine I-2c was synthesized.

MS: m/z 223 ([M+1], $C_{10}H_{10}N_2O_2S$)

Example 17

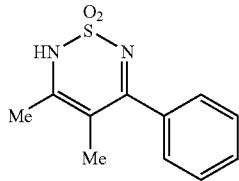
I-2d

Using 2-methyl-1-phenylbutane-1,3-dione as a substrate and by a method similar to that in Example 2, cyclic N-sulfonylimine I-2d was synthesized.

MS: m/z 237 ([M+1], $C_{11}H_{12}N_2O_2S$)

Example 18

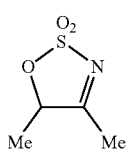
I-3a

Using 3-hydroxy-2-butanone as a substrate and by a method similar to that in Example 1, cyclic N-sulfonylimine I-3a was synthesized.

MS: m/z 150 ([M+1], $C_4H_7NO_3S$)

$^1$H NMR (CDCl$_3$) δ 1.60 (d, 3H, J=6.6 Hz), 2.34 (s, 3H), 5.29 (q, 1H, J=6.6 Hz).

Example 19

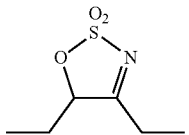
I-3b

Using 4-hydroxy-3-hexanone as a substrate and by a method similar to that in Example 1, cyclic N-sulfonylimine I-3b was synthesized.

MS: m/z 178 ([M+1], $C_6H_{11}NO_3S$)

Example 20

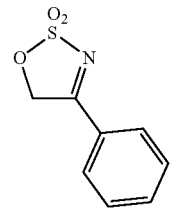
I-3c

Using 2'-hydroxyacetophenone as a substrate and by a method similar to that in Example 1, cyclic N-sulfonylimine I-3c was synthesized.

MS: m/z 198 ([M+1], $C_8H_7NO_3S$)

Example 21

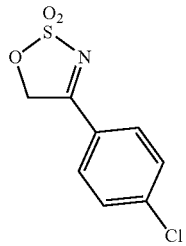
I-3d

Using 4-chloro-2'-hydroxyacetophenone as a substrate and by a method similar to that in Example 1, cyclic N-sulfonylimine I-3d was synthesized.

MS: m/z 232 ([M+1], $C_8H_6ClNO_3S$)

$^1$H NMR (CDCl$_3$) δ 5.39 (s, 2H), 7.47 (d, 2H, J=8.8 Hz), 7.86 (d, 2H, J=8.8 Hz).

Example 22

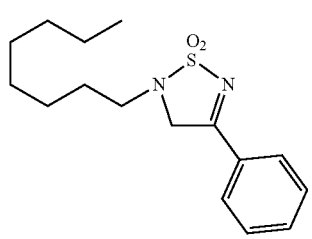
I-3e

Using 4-chloro-2'-octylaminoacetophenone as a substrate and by a method similar to that in Example 1, cyclic N-sulfonylimine I-3e was synthesized.

MS: m/z 309 ([M+1], $C_{16}H_{24}N_2O_2S$)

Example 23

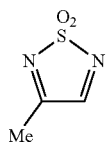

I-4a

Using 2-oxopropionaldehyde as a substrate and by a method similar to that in Example 2, cyclic N-sulfonylimine I-4a was synthesized.

MS: m/z 133 ([M+1], $C_3H_4N_2O_2S$)

Example 24

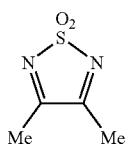

I-4b

Using 2,3-butanedione as a substrate and by a method similar to that in Example 2, cyclic N-sulfonylimine I-4b was synthesized.

MS: m/z 147 ([M+1], $C_4H_6N_2O_2S$)

Example 25

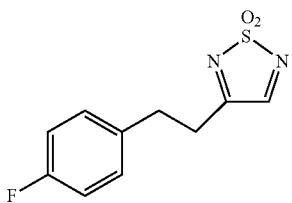

I-4c

Using 4-(4-fluorophenyl)-2-oxobutanal as a substrate and by a method similar to that in Example 2, cyclic N-sulfonylimine I-4c was synthesized.

MS: m/z 241 ([M+1], $C_{10}H_9FN_2O_2S$)

Example 26

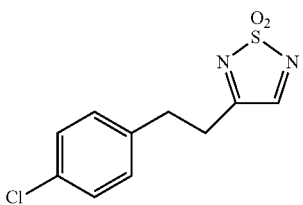

I-4d

Using 4-(4-chlorophenyl)-2-oxobutanal as a substrate and by a method similar to that in Example 2, cyclic N-sulfonylimine I-4d was synthesized.

MS: m/z 257 ([M+1], $C_{10}H_9ClN_2O_2S$)

Example 27

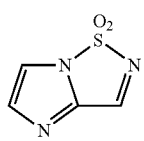

I-5a

Using imidazole-2-carboxyaldehyde as a substrate and by a method similar to that in Example 1, cyclic N-sulfonylimine I-5a was synthesized.

MS: m/z 158 ([M+1], $C_4H_3N_3O_2S$)

Example 28

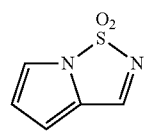

I-5b

Using pyrrole-2-carboxyaldehyde as a substrate and by a method similar to that in Example 1, cyclic N-sulfonylimine I-5b was synthesized.

MS: m/z 157 ([M+1], $C_5H_4N_2O_2S$)

Example 29

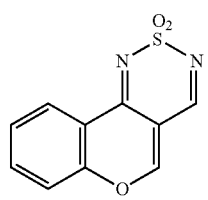

I-6a

Using 4-oxo-4H-chromene-3-carboxyaldehyde as a substrate and by a method similar to that in Example 2, cyclic N-sulfonylimine I-6a was synthesized.

MS: m/z 235 ([M+1], $C_{10}H_6N_2O_3S$)

Example 30

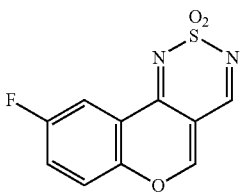

I-6b

Using 6-fluoro-4-oxo-4H-chromene-3-carboxyaldehyde as a substrate and by a method similar to that in Example 2, cyclic N-sulfonylimine I-6b was synthesized.

MS: m/z 253 ([M+1], $C_{10}H_5FN_2O_3S$)

Example 31

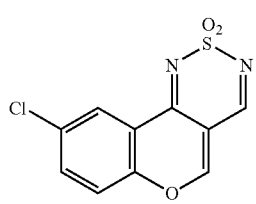

I-6c

Using 6-chloro-4-oxo-4H-chromene-3-carboxyaldehyde as a substrate and by a method similar to that in Example 2, cyclic N-sulfonylimine I-6c was synthesized.

MS: m/z 269 ([M+1], $C_{10}H_5ClN_2O_3S$)

Example 32

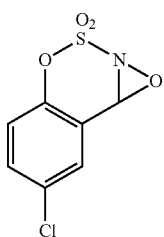

II-1b

Using cyclic N-sulfonylimine I-1b as a substrate and by a method similar to that in Example 3, cyclic N-sulfonyloxaziridine II-1b was synthesized.

MS: m/z 234 ([M+1], $C_7H_4ClNO_4S$)

$^1$H NMR (CDCl$_3$) δ 5.36 (s, 1H), 7.18 (d, 1H, J=8.8 Hz), 7.57 (dd, 1H, J=2.4, 8.8 Hz), 7.69 (d, 1H, J=2.4 Hz).

Example 33

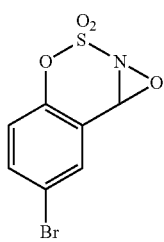

II-1c

Using cyclic N-sulfonylimine I-1c as a substrate and by a method similar to that in Example 3, cyclic N-sulfonyloxaziridine II-1c was synthesized.

MS: m/z 278 ([M+1], $C_7H_4BrNO_4S$)

Example 34

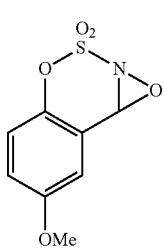

II-1d

Using cyclic N-sulfonylimine I-1d as a substrate and by a method similar to that in Example 3, cyclic N-sulfonyloxaziridine II-1d was synthesized.

MS: m/z 230 ([M+1], $C_8H_7NO_5S$)

$^1$H NMR (CDCl$_3$) δ 3.81 (s, 3H), 5.33 (s, 1H), 7.05 (dd, 1H, J=2.4, 8.8 Hz), 7.13 (d, 1H, J=8.8 Hz), 7.17 (d, 1H, J=2.4 Hz).

Example 35

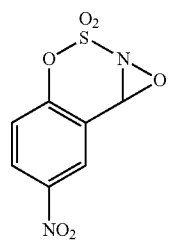

II-1e

Using cyclic N-sulfonylimine I-1e as a substrate and by a method similar to that in Example 3, cyclic N-sulfonyloxaziridine II-1e was synthesized.

MS: m/z 245 ([M+1], $C_7H_4N_2O_6S$)

Example 36

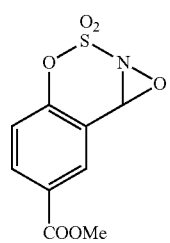

II-1f

Using cyclic N-sulfonylimine I-1f as a substrate and by a method similar to that in Example 3, cyclic N-sulfonyloxaziridine II-1f was synthesized.

MS: m/z 258 ([M+1], $C_9H_7NO_6S$)

Example 37

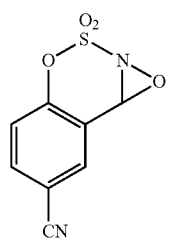

II-1g

Using cyclic N-sulfonylimine I-1g as a substrate and by a method similar to that in Example 3, cyclic N-sulfonyloxaziridine II-1g was synthesized.

MS: m/z 225 ([M+1], $C_8H_4N_2O_4S$)

Example 38

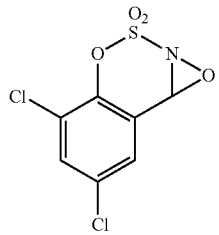
II-1h

Using cyclic N-sulfonylimine I-1h as a substrate and by a method similar to that in Example 3, cyclic N-sulfonyloxaziridine II-1h was synthesized.
MS: m/z 268 ([M+1], $C_7H_3Cl_2NO_4S$)

Example 39

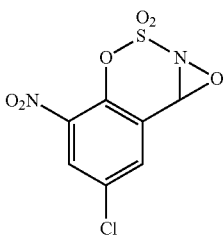
II-1i

Using cyclic N-sulfonylimine I-1i as a substrate and by a method similar to that in Example 3, cyclic N-sulfonyloxaziridine II-1i was synthesized.
MS: m/z 279 ([M+1], $C_7H_3ClN_2O_6S$)

Example 40

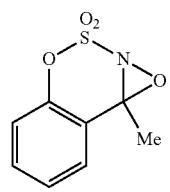
II-1j

Using cyclic N-sulfonylimine I-1j as a substrate and by a method similar to that in Example 3, cyclic N-sulfonyloxaziridine II-1j was synthesized.
MS: m/z 214 ([M+1], $C_8H_7NO_4S$)

Example 41

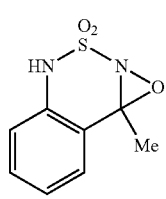
II-1k

Using cyclic N-sulfonylimine I-1k as a substrate and by a method similar to that in Example 3, cyclic N-sulfonyloxaziridine II-1k was synthesized.
MS: m/z 213 ([M+1], $C_8H_8N_2O_3S$)

Example 42

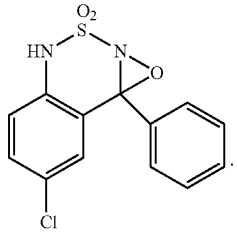
II-1l

Using cyclic N-sulfonylimine I-1l as a substrate and by a method similar to that in Example 3, cyclic N-sulfonyloxaziridine II-1l was synthesized.
MS: m/z 309 ([M+1], $C_{13}H_9ClN_2O_3S$)

Example 43

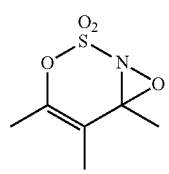
II-2a

Using cyclic N-sulfonylimine I-2a as a substrate and by a method similar to that in Example 3, cyclic N-sulfonyloxaziridine II-2a was synthesized.
MS: m/z 192 ([M+1], $C_6H_9NO_4S$)

Example 44

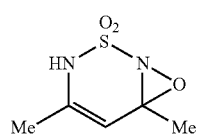
II-2b

Using cyclic N-sulfonylimine I-2b as a substrate and by a method similar to that in Example 3, cyclic N-sulfonyloxaziridine II-2b was synthesized.
MS: m/z 177 ([M+1], $C_5H_8N_2O_3S$)

Example 45

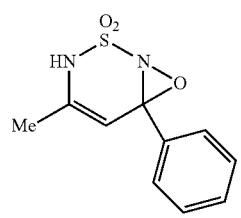
II-2c

Using cyclic N-sulfonylimine I-2c as a substrate and by a method similar to that in Example 3, cyclic N-sulfonyloxaziridine II-2c was synthesized.

MS: m/z 239 ([M+1], $C_{10}H_{10}N_2O_3S$)

Example 46

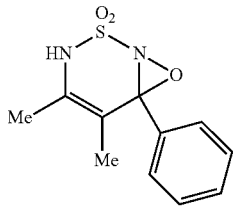
II-2d

Using cyclic N-sulfonylimine I-2d as a substrate and by a method similar to that in Example 3, cyclic N-sulfonyloxaziridine II-2d was synthesized.

MS: m/z 253 ([M+1], $C_{11}H_{12}N_2O_3S$)

Example 47

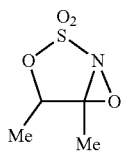
II-3a

Using cyclic N-sulfonylimine I-3a as a substrate and by a method similar to that in Example 3, cyclic N-sulfonyloxaziridine II-3a was synthesized.

MS: m/z 166 ([M+1], $C_4H_7NO_4S$)

$^1$H NMR (CDCl$_3$) δ 1.67 (d, 3H, J=6.6 Hz), 1.61 (s, 3H), 5.12 (q, 1H, J=6.6 Hz).

Example 48

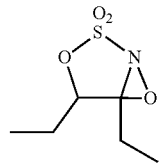
II-3b

Using cyclic N-sulfonylimine I-3b as a substrate and by a method similar to that in Example 3, cyclic N-sulfonyloxaziridine II-3b was synthesized.

MS: m/z 194 ([M+1], $C_6H_{11}NO_4S$)

Example 49

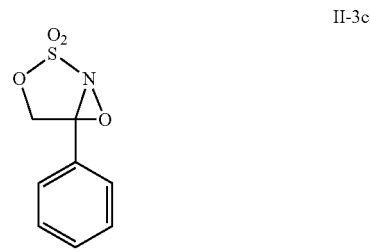 [SMILES: O=S1(=O)OCC2(c3ccccc3)ON21]
II-3c

Using cyclic N-sulfonylimine I-3c as a substrate and by a method similar to that in Example 3, cyclic N-sulfonyloxaziridine II-3c was synthesized.

MS: m/z 214 ([M+1], $C_8H_7NO_4S$)

Example 50

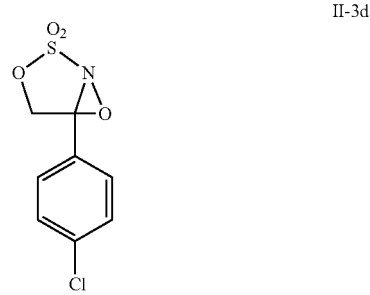 [SMILES: O=S1(=O)OCC2(c3ccc(Cl)cc3)ON21]
II-3d

Using cyclic N-sulfonylimine I-3d as a substrate and by a method similar to that in Example 3, cyclic N-sulfonyloxaziridine II-3d was synthesized.

MS: m/z 248 ([M+1], $C_8H_6ClNO_4S$)

Example 51

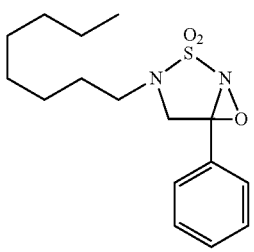
II-3e

Using cyclic N-sulfonylimine I-3e as a substrate and by a method similar to that in Example 3, cyclic N-sulfonyloxaziridine II-3e was synthesized.

MS: m/z 325 ([M+1], $C_{16}H_{24}N_2O_3S$)

Example 52

II-4a

Using cyclic N-sulfonylimine I-4a as a substrate and by a method similar to that in Example 3, cyclic N-sulfonyloxaziridine II-4a was synthesized.
MS: m/z 149 ([M+1], $C_3H_4N_2O_3S$)

Example 53

II-4b

Using cyclic N-sulfonylimine I-4b as a substrate and by a method similar to that in Example 3, cyclic N-sulfonyloxaziridine II-4b was synthesized.
MS: m/z 163 ([M+1], $C_4H_6N_2O_3S$)

Example 54

II-4c

Using cyclic N-sulfonylimine I-4c as a substrate and by a method similar to that in Example 3, cyclic N-sulfonyloxaziridine II-4c was synthesized.
MS: m/z 257 ([M+1], $C_{10}H_9FN_2O_3S$)

Example 55

II-4d

Using cyclic N-sulfonylimine I-4d as a substrate and by a method similar to that in Example 3, cyclic N-sulfonyloxaziridine II-4d was synthesized.
MS: m/z 273 ([M+1], $C_{10}H_9ClN_2O_3S$)

Example 56

II-5a

Using cyclic N-sulfonylimine I-5a as a substrate and by a method similar to that in Example 3, cyclic N-sulfonyloxaziridine II-5a was synthesized.
MS: m/z 174 ([M+1], $C_4H_3N_3O_3S$)

Example 57

II-5b

Using cyclic N-sulfonylimine I-5b as a substrate and by a method similar to that in Example 3, cyclic N-sulfonyloxaziridine II-5b was synthesized.
MS: m/z 173 ([M+1], $C_5H_4N_2O_3S$)

Example 58

II-6a

Using cyclic N-sulfonylimine I-6a as a substrate and by a method similar to that in Example 3, cyclic N-sulfonyloxaziridine II-6a was synthesized.
MS: m/z 251 ([M+1], $C_{10}H_6N_2O_4S$)

Example 59

II-6b

Using cyclic N-sulfonylimine I-6b as a substrate and by a method similar to that in Example 3, cyclic N-sulfonyloxaziridine II-6b was synthesized.

MS: m/z 269 ([M+1], $C_{10}H_5FN_2O_4S$)

Example 60

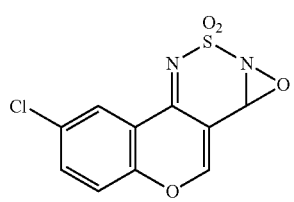

II-6c

Using cyclic N-sulfonylimine I-6c as a substrate and by a method similar to that in Example 3, cyclic N-sulfonyloxaziridine II-6c was synthesized.

MS: m/z 285 ([M+1], $C_{10}H_5ClN_2O_4S$)

Experimental Example

Measurement Method of Antifungal Activity in Various Compounds

The minimum inhibitory concentration (MIC) was measured by a disc method (diffusion method). The disc method is one kind of the diffusion method, and is a method in which filter paper (disc) impregnated with an antifungal substance at a given concentration is placed on an agar medium (test plate) coated with a test bacterium and cultivated. The disc absorbs water in the medium, diffuses the antifungal substance and forms a given concentration gradient. As a result, the test bacterium forms a growth inhibition zone (circle) in the periphery of the disc, and the level of sensitivity to the antifungal substance is determined from the diameter of the inhibition circle.

Using the aforementioned method, MIC of various compounds was measured.

[Measurement Method]
1. Preculture
   i: In a 100 mL flask, 20 mL of YMG or Mueller Hinton medium is produced.
   ii: A loopful of the test bacterium is dissolved in the medium.
   iii: The medium is cultured at 200 rpm for 24 hr in a rotary shaker set to 28° C.
2. Test Plate Production
   i: In a 300 mL flask, 100 mL of YMG or Mueller Hinton agar medium (low melting point agar) is produced.
   ii: After cooling to 37° C.-40° C., preculture medium (1 mL) is added and the mixture is agitated.
   iii: The mixture is dispensed to a square petri dish (size: 100*150*17 mm) by 20 mL each.
   iv: The dish is stood at room temperature until the agar is solidified.
3. Test and Measurement
   i: The compound is diluted in ½ dilution series in 10 stages (timely changed according to compound), 50 μL of solution/pulp at each dilution stage is produced, the organic solvent is dried at room temperature and placed on a test plate.
   ii: After culturing *T. rubrum* for 48 hr and other test bacteria for 24 hr at 28° C. in an incubator, the size of the inhibition circle was measured.

The medium composition for culture which was used for the aforementioned preculture is shown below.
[Medium Compositions for Preculture and Test Plate]
<<YMG Medium>>: For Fungus
   Yeast extract 0.3%
   Peptone 0.5%
   Malt extract 0.3%
   Glucose 1%
   Agar, powder 0.8% * added only when producing test plate
<<Mueller Hinton Medium>>: For Bacterium
   Mueller Hinton Broth 2.1%
   Agar, powder 0.8% * added only when producing test plate The obtained MIC values (μg/mL) are shown in the following Table.

TABLE 1

| compound | Saccharomyces | C. parapsilosis | T. mentagrophytes | T. rubrum | A. fumigatus |
| --- | --- | --- | --- | --- | --- |
| I-1a | 4 | 4 | 1 | 1 | 4 |
| I-1b | 4 | 4 | 1 | 1 | 4 |
| I-1c | 4 | 4 | 1 | 1 | 4 |
| I-1d | 8 | 8 | 2 | 2 | 8 |
| I-1e | 4 | 4 | 1 | 1 | 4 |
| I-1f | 4 | 4 | 1 | 1 | 4 |
| I-1g | 4 | 4 | 1 | 1 | 4 |
| I-1h | 4 | 4 | 1 | 1 | 4 |
| I-1i | 4 | 4 | 1 | 1 | 4 |
| I-1j | 8 | 8 | 2 | 2 | 8 |
| I-1k | 8 | 8 | 2 | 2 | 8 |
| I-1l | 8 | 8 | 2 | 2 | 8 |
| I-2a | 8 | 8 | 2 | 2 | 8 |
| I-2b | 16 | 16 | 2 | 2 | 16 |
| I-2c | 8 | 8 | 2 | 2 | 8 |
| I-2d | 8 | 8 | 2 | 2 | 8 |
| I-3a | 4 | 4 | 2 | 2 | 4 |
| I-3b | 4 | 4 | 2 | 2 | 4 |
| I-3c | 8 | 8 | 2 | 2 | 8 |
| I-3d | 8 | 8 | 2 | 2 | 8 |
| I-3e | 8 | 8 | 2 | 2 | 8 |

TABLE 1-continued

| compound | Saccharomyces | C. parapsilosis | T. mentagrophytes | T. rubrum | A. fumigatus |
|---|---|---|---|---|---|
| I-4a | 8 | 8 | 2 | 2 | 8 |
| I-4b | 16 | 16 | 4 | 4 | 16 |
| I-4c | 8 | 8 | 2 | 2 | 8 |
| I-4d | 8 | 8 | 2 | 2 | 8 |
| I-5a | 8 | 8 | 2 | 2 | 8 |
| I-5b | 16 | 16 | 4 | 4 | 16 |
| I-6a | 4 | 4 | 1 | 1 | 4 |
| I-6b | 4 | 4 | 1 | 1 | 4 |
| I-6c | 4 | 4 | 1 | 1 | 4 |
| II-1a | 4 | 4 | 1 | 1 | 4 |
| II-1b | 4 | 4 | 1 | 1 | 4 |
| II-1c | 4 | 4 | 1 | 1 | 4 |
| II-1d | 8 | 8 | 2 | 2 | 8 |
| II-1e | 4 | 4 | 1 | 1 | 4 |
| II-1f | 4 | 4 | 1 | 1 | 4 |
| II-1g | 4 | 4 | 1 | 1 | 4 |
| II-1h | 4 | 4 | 1 | 1 | 4 |
| II-1i | 4 | 4 | 1 | 1 | 4 |
| II-1j | 8 | 8 | 2 | 2 | 8 |
| II-1k | 8 | 8 | 2 | 2 | 8 |
| II-1l | 8 | 8 | 2 | 2 | 8 |
| II-2a | 8 | 8 | 2 | 2 | 8 |
| II-2b | 16 | 16 | 2 | 2 | 16 |
| II-2c | 8 | 8 | 2 | 2 | 8 |
| II-2d | 8 | 8 | 2 | 2 | 8 |
| II-3a | 4 | 4 | 2 | 2 | 4 |
| II-3b | 4 | 4 | 2 | 2 | 4 |
| II-3c | 8 | 8 | 2 | 2 | 8 |
| II-3d | 8 | 8 | 2 | 2 | 8 |
| II-3e | 8 | 8 | 2 | 2 | 8 |
| II-4a | 8 | 8 | 2 | 2 | 8 |
| II-4b | 16 | 16 | 4 | 4 | 16 |
| II-4c | 8 | 8 | 2 | 2 | 8 |
| II-4d | 8 | 8 | 2 | 2 | 8 |
| II-5a | 8 | 8 | 2 | 2 | 8 |
| II-5b | 16 | 16 | 4 | 4 | 16 |
| II-6a | 4 | 4 | 1 | 1 | 4 |
| II-6b | 4 | 4 | 1 | 1 | 4 |
| II-6c | 4 | 4 | 1 | 1 | 4 |

INDUSTRIAL APPLICABILITY

According to the present invention, an antifungal composition containing a cyclic N-sulfonylamine compound, a cyclic N-sulfonylimine compound or a cyclic N-sulfonyloxaziridine compound, each having an antifungal activity, as an active ingredient is provided.

This application is based on patent application No. 2017-035508 filed in Japan, the contents of which are encompassed in full herein.

The invention claimed is:

1. An antifungal composition comprising a compound of formula:

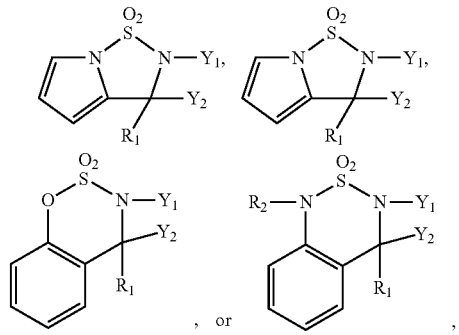

wherein
the pyrrole ring, imidazole ring, or benzene ring is optionally substituted, $Y_1$ and $Y_2$ are joined to form a bond, $R_1$ is a hydrogen atom, a $C_{1-20}$ alkyl group, or a $C_{6-20}$ aryl group, $R_2$ is a hydrogen atom, and optional substituents are independently selected from a halogen atom, a nitro group, a cyano group, a $C_{1-6}$ alkoxy group, and a $C_{1-6}$ alkoxy-carbonyl group.

2. The antifungal composition according to claim 1, wherein the antifungal composition comprises the compound of formula:

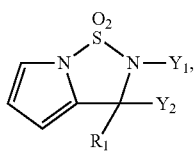

wherein the pyrrole ring is optionally substituted, and
wherein each symbol and the optional substituents are as defined in claim 1.

3. The antifungal composition according to claim 1, wherein the antifungal composition comprises the compound of formula:

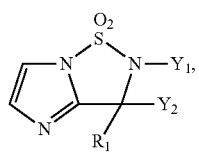

wherein the imidazole ring is optionally substituted, and
wherein each symbol and the optional substituents are as defined in claim 1.

4. The antifungal composition according to claim 1, wherein the antifungal composition comprises the compound of formula:

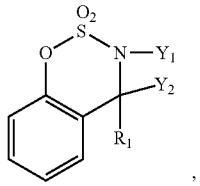

wherein the benzene ring is optionally substituted, and
wherein each symbol and the optional substituents are as defined in claim 1.

5. The antifungal composition according to claim 1, wherein the antifungal composition comprises the compound of formula:

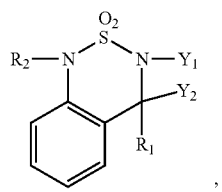

wherein the benzene ring is optionally substituted, and
wherein each symbol and the optional substituents are as defined in claim 1.

6. The antifungal composition according to claim 1, wherein $R_1$ is a hydrogen atom.

7. The antifungal composition according to claim 1, wherein $R_1$ is a $C_{1-20}$ alkyl group.

8. The antifungal composition according to claim 1, wherein $R_1$ is a $C_{6-20}$ aryl group.

9. The antifungal composition according to claim 2, wherein $R_1$ is a hydrogen atom.

10. The antifungal composition according to claim 2, wherein $R_1$ is a $C_{1-20}$ alkyl group.

11. The antifungal composition according to claim 2, wherein $R_1$ is a $C_{6-20}$ aryl group.

12. The antifungal composition according to claim 3, wherein $R_1$ is a hydrogen atom.

13. The antifungal composition according to claim 3, wherein $R_1$ is a $C_{1-20}$ alkyl group.

14. The antifungal composition according to claim 3, wherein $R_1$ is a $C_{6-20}$ aryl group.

15. The antifungal composition according to claim 4, wherein $R_1$ is a hydrogen atom.

16. The antifungal composition according to claim 4, wherein $R_1$ is a $C_{1-20}$ alkyl group.

17. The antifungal composition according to claim 4, wherein $R_1$ is a $C_{6-20}$ aryl group.

18. The antifungal composition according to claim 5, wherein $R_1$ is a hydrogen atom.

19. The antifungal composition according to claim 5, wherein $R_1$ is a $C_{1-20}$ alkyl group.

20. The antifungal composition according to claim 5, wherein $R_1$ is a $C_{6-20}$ aryl group.

* * * * *